(12) United States Patent
Cohen et al.

(10) Patent No.: US 11,253,679 B2
(45) Date of Patent: Feb. 22, 2022

(54) MEDICAL DEVICE MANAGEMENT SYSTEM

(71) Applicant: NEXUS CONTROL SYSTEMS, LLC, Port Washington, NY (US)

(72) Inventors: Todd J. Cohen, Port Washington, NY (US); John R. Lubisich, West Linn, OR (US); Gregory Morrison, Tualatin, OR (US); Michael Morrison, Tualatin, OR (US)

(73) Assignee: Nexus Control Systems, LLC, Port Washington, NY (US)

( * ) Notice: Subject to any disclaimer, the term of this patent is extended or adjusted under 35 U.S.C. 154(b) by 7 days.

(21) Appl. No.: 15/147,538

(22) Filed: May 5, 2016

(65) Prior Publication Data

US 2017/0361067 A1   Dec. 21, 2017

Related U.S. Application Data

(63) Continuation-in-part of application No. 14/215,333, filed on Mar. 17, 2014, now Pat. No. 10,143,825.

(60) Provisional application No. 61/787,391, filed on Mar. 15, 2013.

(51) Int. Cl.
| | |
|---|---|
| *A61M 25/02* | (2006.01) |
| *A61N 1/05* | (2006.01) |
| *A61B 90/50* | (2016.01) |
| *A61B 90/57* | (2016.01) |

(52) U.S. Cl.
CPC ............. *A61M 25/02* (2013.01); *A61B 90/50* (2016.02); *A61B 90/57* (2016.02); *A61N 1/05* (2013.01); *A61M 2025/0253* (2013.01); *A61M 2025/0273* (2013.01); *A61M 2205/583* (2013.01)

(58) Field of Classification Search
CPC .......... A61M 25/02; A61M 2025/0246; A61M 2025/0253; A61M 2025/026; A61M 2025/0266; A61M 2025/0273; A61M 2025/0213; A61M 2025/0206; A61M 2025/024; A61M 3/027
See application file for complete search history.

(56) References Cited

U.S. PATENT DOCUMENTS

| | | | | |
|---|---|---|---|---|
| 5,238,010 A | * | 8/1993 | Grabenkort | A61M 25/02 128/846 |
| 5,643,217 A | * | 7/1997 | Dobkin | A61B 17/00 604/174 |
| 6,244,265 B1 | * | 6/2001 | Cronk | A61F 5/08 128/200.24 |
| 2006/0167417 A1 | * | 7/2006 | Kratz | A61M 25/0668 604/164.05 |

(Continued)

*Primary Examiner* — Nilay J Shah
(74) *Attorney, Agent, or Firm* — William H. Dippert; Laurence A. Greenberg; Werner H. Stemer

(57) ABSTRACT

A medical device or catheter management system comprises several layers where a top layer has one or more channels to receive one or more elongated medical devices or members and a bottom layer comprises adhesive to secure the catheter management system to a patient or other secure site in the operating field. A firm upper surface causes the elongated medical devices or members to stay in the channels, whereas a firm inner layer facilitates maintaining the shape of the catheter management system and providing resistance for an operator to easily release an elongated medical device or member.

21 Claims, 12 Drawing Sheets

(56) References Cited

U.S. PATENT DOCUMENTS

2010/0010475 A1* 1/2010 Teirstein ............... A61M 25/02
604/528

* cited by examiner

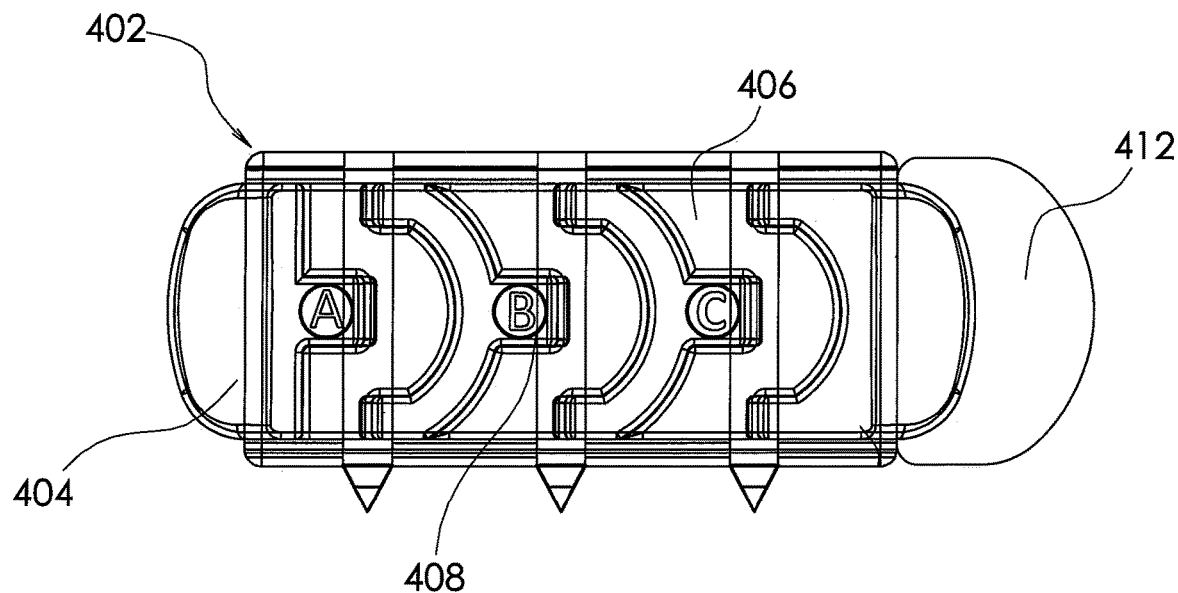
FIG. 12A
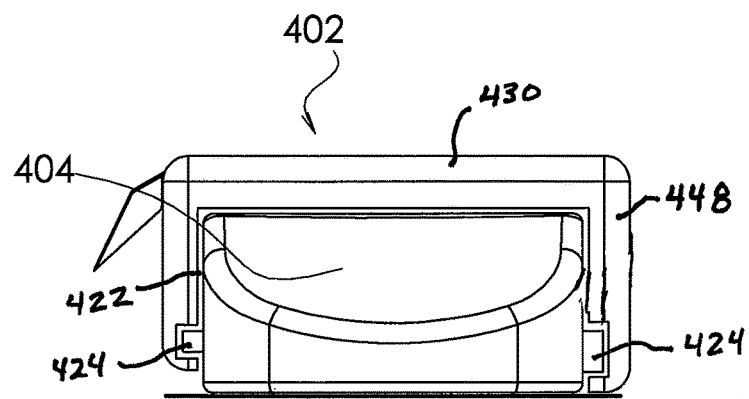
FIG. 12B
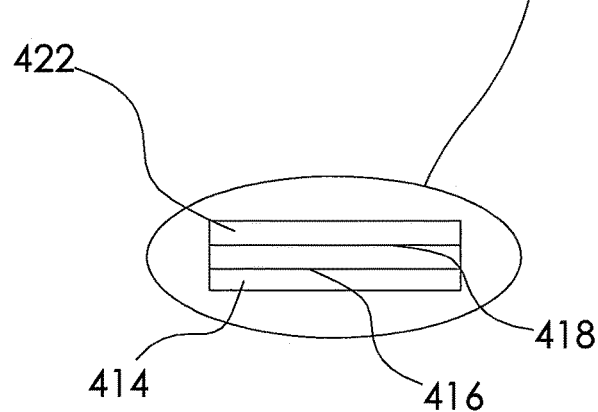

MEDICAL DEVICE MANAGEMENT SYSTEM

CROSS-REFERENCE TO RELATED PATENT APPLICATIONS

This application is a continuation-in-part of co-pending, commonly assigned U.S. patent application Ser. No. 14/215,333, filed Mar. 17, 2014, which in turn is based upon and claims the benefit of the filing date of, commonly assigned U.S. Provisional Patent Application Ser. No. 61/787,391, filed Mar. 15, 2013, each of which is incorporated herein by reference in its entirety.

FIELD OF THE INVENTION

This patent application is directed to a medical device or catheter management system. More particularly, this patent application is directed to a medical device or catheter management system comprising a flexible substrate having at least one layer and one or more grooves, slots, slits, channels, or openings to receive and release elongated medical devices or members such as catheters, guide wires, leads, sheaths, and the like, used for surgical or intravascular medical procedures. The medical device or catheter management system's primary function is to be attached near or on a patient to hold a variety of elongated medical devices or members in position and to easily release said elongated medical devices or members for repositioning and/or removal.

BACKGROUND OF THE INVENTION

When procedures are performed on a patient in a catheterization lab, an electrophysiology laboratory, or an interventional radiology or operative suite, a number of longitudinally extending, or elongated, medical devices or members are employed. Dependent upon which procedure is being performed, any number of catheters, guide wires, guiding catheters, sheaths, leads, medical tubing, or other elongated medical devices or members can be used. These elongated medical devices or members are primarily very long thin tubes or rods that may come in a variety of lengths and widths. The operator has the responsibility to carefully manipulate these elongated medical devices or members in sometimes very complex procedures. Once the device or member reaches the desired position, it is often necessary and sometimes critical to maintain that position, to perform a specific task or procedure, or to free up one's hands such that other tasks can be performed.

In some of the procedures it is necessary to insert one elongated medical device or member into a patient and then to keep that elongated medical device or member in position while an operator inserts or retracts another elongated medical device or member. As mentioned above, the operator may also want to secure one or more elongated medical devices or members while the operator frees up his or her hands to perform other tasks. As a result, there can be a number of coextensively extending elongated medical devices or members where the relative positions have to be maintained. At the present time, it is part of an operator's technique to maintain the respective elongated medical devices or members in desired relationships to one another. This may require multiple individuals to hold these devices or members in position concurrently. If not, the other devices or members may shift positions and require repositioning, lengthening the procedure.

The management of coextensively extending elongated medical devices or members is a concern during, for example, an electrophysiology study or a catheter ablation procedure. Typically a number of catheters, guide wires, or sheaths are placed through either veins or arteries into a variety of locations within the heart. The catheters can, for example, record specific potentials, and they often move out of place. This movement is due to the fact that standard introducer sheaths only provide a small amount of resistance and patient and/or catheter movement during the procedure can easily dislodge a catheter tip's position. Also, a patient may move his or her body or legs when shocked or due to discomfort. In addition, sometimes the patient goes into a life threatening arrhythmia such as ventricular tachycardia or ventricular fibrillation in which high voltage energy needs to be delivered to the patient through external patches. When this occurs, the patient often jerks or kicks as a result of muscular contraction, often dislodging the catheters or leads. The catheters or leads then need to be put back in place to go on with the procedure. Sometimes a more bulky and expensive "lock-down" sheath can be used to prevent catheter movement; however, this is impractical for use in procedures that require multiple catheters (since that would require a more expensive "lock-down" sheath be used for every catheter inserted). Having to reposition catheters, guide wires, or sheaths adds time to a procedure and increases radiation exposure.

At times an operator must deliver and keep a flexible elongated medical device or member in a fixed position either through a single blood vessel or through two or more blood vessels, which terminate in a single vascular structure. In one circumstance, an operator passes two or more pairs of flexible elongated medical devices or members through the same blood vessel, either directly via a cut-down procedure, though a single introducer, or through a Y-adaptor. The multiple flexible elongated medical devices or members travel down a single or multiple veins and/or arteries such that the elongated medical devices or members are positioned in the heart and circulatory system, either for diagnostic and/or therapeutic purposes. Their apposition, next to each other, may hinder the stable position of one elongated medical device or member, while the other is positioned.

The multiple elongated medical devices or members may be, for example, guide wires, catheters, pacemaker or defibrillator leads, medical tubing of a variety of sorts, or sheaths. Since the elongated medical devices or members may have similar points of entry, such as the right groin for the right femoral artery and vein, an operator must take steps to keep the elongated medical devices or members organized and separate from each other, and to keep each member identified with the location and purpose. It is important to keep the elongated medical devices or members separate for several reasons. If the elongated medical devices or members become twisted, they will interact with one another. For example, when an operator moves one wire or catheter, another wire or catheter may also move out of position. Further, different devices, such as stents, are typically passed over the guide wires on the catheters; therefore, if the wire/catheter pairs become twisted with each other, accurate advancement of the associated devices is hindered. Also, since different devices are passed over the different wires on the catheters, the operator must take steps to identify each wire so as not to confuse which wire is going down which vessel or branch vessel.

During electrophysiology procedures and/or cardiac catheter ablation procedures, multiple catheters are positioned in a single blood vessel such as the right femoral vein and perhaps the right femoral artery, all in proximity to one another. The wires are often placed in very discrete locations to record and diagnose a particular condition. It is not infrequent for four such catheters to be located in one groin location. Movement of the patient could result in catheter movement and require repositioning of the catheter. "Lockdown" introducers are useful, but expensive. There is a need for a simple and inexpensive catheter management system to hold catheters of a variety of shapes in place and for such a system to be able to rapidly and quickly release the catheter(s) for further mapping and repositioning.

Another comparable example of the same effect as described above is implantation of a multi-lead implantable heart rhythm device such as a pacemaker or defibrillator (and a biventricular device typically has three leads). Very frequently, those leads are implanted through a single blood vessel such as the cephalic, auxiliary, or subclavian vein. To prevent the problem of unintended movement, the operator may have to percutaneously stick a second blood vessel, thereby subjecting the patient to additional vascular or pneumothorax risk. In addition, placement of "a third lead" (in addition to the standard right atrial and right ventricular leads) such as the left ventricular lead used in biventricular devices, eventually requires a process of slitting a long sheath, which often may dislodge the previously placed right atrial and ventricular leads. Also, when slitting and removing the delivery sheath of a left ventricular lead, it is desirable to hold and maintain that lead in position, while the sheath is removed. This often requires a second individual and/or repositioning of the left ventricular lead, which may pull back while the sheath is being removed (pulled back as well). These lead movements, displacements, and even dislodgements typically lengthens and complicates these procedures. A method of easily securing leads while positioning another is needed. In addition, a method of securing leads while slitting a deliverable lead is also required. Further, a method of easily releasing the leads for additional positioning is required.

OBJECTS OF THE INVENTION

It is an object of the invention to provide a simple and effective medical device or catheter management system.

It is also an object of the invention to provide a medical device or catheter management system comprised of a flexible substrate wherein an elongated medical device or member such as a catheter, guide wire, sheath, lead, or medical tubing of some sort is positioned in a catheterization lab or a surgical field to maintain the relative positions of the elongated medical devices or members.

It is a further object of the invention to provide a medical device or catheter management system comprising a flexible substrate comprising at least one layer and at least one lateral groove, slot, slit, channel, or opening.

It is a yet further object of the invention to provide a medical device or catheter management system comprising a sterile dual layered system consisting of an upper flexible substrate with grooves, slots, slits, channels, or openings and a lower adhesive layer to adhere to the skin, sterile drape, or any surgically related object or material.

It is a yet further object of the invention to provide a medical device or catheter management system in which the channels or openings are nonlinear.

It is a yet further object of the invention to provide a medical device or catheter management system in which the channel or openings are curvilinear.

It is a yet further object of the invention to provide a medical device or catheter management system in which a perpendicular resistive component (for example, a centrally located resistance-applying prong member) is utilized to create a curvilinear channel and said component provides "pincer-like" resistance to translation and rotation of an elongated medical device or member.

It is a yet further object of the invention to provide pincer resistance within said lateral groove to replicate the resistance typically applied between the operator's thumb and forefinger while holding a catheter or lead in place.

It is a yet further object of the invention to create pincer units of resistance (much like the hand adds additional fingers to provide additional resistance against the thumb, to hold a catheter or lead in place) to handle and control catheter or lead translation and rotation by applying resistive force to the catheter or lead to hold the catheter or lead in place and easily be released for manipulation.

It is a yet further object of the invention to incorporate at least one curvilinear pathway with a thumb-like, firm but slightly flexible prong within the concavity to apply pressure to a catheter or lead member to provide resistance to rotation and translation within the member.

It is a yet further object of the invention to apply the pincer units, consisting of a curvilinear pathway with a centrally located resistance-applying prong member, in parallel, to easily hold and release multiple catheters and leads during invasive procedures.

It is a yet further object of the invention in which the perpendicular resistive components are labeled in a manner to help organize the elongated medical devices or members.

It is a yet further object of the invention to apply multiple parallel pincer units to help organize the multiple catheter, leads, and their cables, tubes, guide wires on a sterile field and prevent entanglement and confusion during a procedure.

It is a yet further object of the invention to apply the pincer units in series (multiple units on a single elongated medical device or member) to apply increased resistance to catheter and/or lead rotation and translation. This configuration is like adding fingers to a hold between the thumb, to prevent rotation and translation of an elongated medical device or member.

It is a yet further object of the invention to apply pincer units in both parallel and series in a single sterile medical device system such that multiple elongated medical devices or members may be held simultaneously, but with different resistive forces applied (determined by the number of pincer units holding a given device or member).

It is a yet further object of the invention to provide a medical device or catheter management system comprising a flexible substrate comprising at least two layers and at least one groove, slot, slit, channel, or opening.

It is a yet further object of the invention to provide a medical device or catheter management system comprising a flexible substrate comprising at least three layers and at least one or more grooves, slots, slits, channels, or openings.

It is a yet further object of the invention to provide an alternate base to the bottom or lower surface of the medical device or catheter management system to adhere to a sterile field during a procedure.

It is a yet further object of the invention to provide a medical device or catheter management system comprising a flexible substrate comprising at least two layers and at least one lateral groove, slot, slit, channel, or opening.

It is a yet further object of the invention to provide a medical device or catheter management system comprising a flexible substrate comprising at least three layers and at least one or more lateral grooves, slots, slits, channels, or openings.

It is a yet further object of the invention to provide an alternate base to the bottom or lower surface of the medical device or catheter management system to adhere to a sterile field during a procedure.

It is a yet further object to provide printed material on the top surface of the medical device or catheter management system to instruct, warn, market, promote, and/or advertise.

It is a yet further object to provide a device to free up an operator's hand to perform other functions or tasks without losing progress made in positioning a catheter, guide wire, sheath, lead, medical tubing of some sort, or other elongated medical device or member.

It is a yet further object to provide a device to allow an operator to grab and manipulate a catheter, sheath, wire, lead, medical tubing of some sort, or other elongated medical device or member without having to take multiple steps to release a catheter, sheath, guide wire, lead, or other elongated medical device or member from a securing device.

It is a yet further object to provide comfort to an operator's hand during a procedure by allowing the operator to use less finger strength to maneuver a catheter, sheath, guide wire, lead, medical tubing of some sort, or other elongated medical device or member than would normally be required.

It is a yet further object of the invention to provide a medical device or catheter management system that comprises a single elongated substrate having one or more channels or grooves that each extend laterally and are configured to releasably hold an elongated flexible medical device.

It is a yet further object of the invention to provide a device for managing one or more elongated medical devices, comprising an elongated substrate having one or more grooves or channels, each extending from a first lateral surface to a second lateral surface, wherein each groove or channel has a depth sufficient to receive an elongated medical device and the groove or channel comprises one or more protrusions, substances, or both capable of releasably holding the elongated medical device.

These and other objects of the invention will become more apparent from the discussion below.

SUMMARY OF THE INVENTION

The medical device or catheter management system (CMS) described below is a simple, inexpensive, and useful tool which, because of its design, can easily hold and release a variety of catheters, guide wires, implantable leads, sheaths, and other elongated medical devices or members, such as, for example, intravenous, intraarterial, intrapericardial, intrathoracic, intraperitoneal, intraurinary, internal, infusion, or drainage tubing. The purpose of this system is to hold and organize elongated medical devices as well as to organize them. To provide this functionality, a simple disposable medical device having an adhesive component has been developed to hold a variety of elongated medical devices or members of different sizes in place, organize their purpose, and provide for easy release during repositioning and/or removal. Traditionally the thumb and forefinger provide a pincer function as they apply a force to a catheter or lead to hold them manually in place. A medical device or catheter management system has been developed which mimics the pincer function of the human hand. These pincer units consist of a channel, for example, a concave curvilinear channel with a centrally oriented rod component which applies a perpendicular pressure to the catheter or lead member once placed within the channel to prevent rotation and translation of the elongated medical device or member. Each pincer member's rotation and translational resistance can be quantified. Parallel configurations of these members can permit the easy holding and release of multiple elongated medical devices or members, for example, catheters and/or leads. Series configurations (in which multiple pincer units grip a single elongated medical device or member) can amplify the holding resistance and further prevent rotation and translation of a catheter or lead member. One can look at this much like the pincer function of the human hand, in which the forefinger and thumb can grip an elongated medical device or member. Adding an additional finger can augment the holding resistance and prevent rotation and translation of said elongated medical device or member.

In another aspect of the invention, the catheter management system is comprised of pincer units that mimic the function of the thumb and forefinger in which a nonlinear or curvilinear channel has a centrally located perpendicular resistance prong to provide a place for inserting and holding an elongated medical device or member. The placement of an elongated medical device or member in the CMS is not a linear function but a procedure in which the elongated medical device or member is carefully introduced into or positioned within the CMS in a manner that does not distort or damage the elongated medical device or member.

In another aspect of the invention, a medical device or catheter management system has been designed to assist an operator in a catheterization lab, although the catheter management system could be useful in other hospital or operating situations, such as an operating room, an electrophysiology laboratory, or an interventional radiology suite. The catheter management system comprises a pliable or flexible substrate or pad having at least one groove, slot, slit, gap, or opening, that is, a channel, capable of holding a catheter, guide wire, lead, sheath, or other elongated medical device or member of various shapes and sizes. Upon downward pressure the channel gives permitting it to receive a catheter, guide wire, lead, sheath, medical tubing of some sort, or other elongated medical device or member to close or form around the catheter, guide wire, lead, sheath, or other elongated medical device or member. The catheter, guide wire, lead, sheath, or other elongated medical device or member is held in the channel until the operator gently urges the catheter, guide wire, lead, sheath, or other elongated medical device or member upward to release it from the channel.

In one embodiment of the invention, the medical device or catheter management system essentially comprises two layers or components, a first layer or component, preferably with varying firmness, to receive one or more catheters, guide wires, leads, sheaths, or other elongated medical devices or members and a second layer or component having an adhesive backing or surface to affix or attach the catheter management system to a suitable surface, such as the patient's skin, a sterile drape, an operating table, or a gurney. It is within the scope of the invention that there could be one or more additional layers, such as an upper, slightly rigid layer atop the first layer or a slightly rigid layer between the first flexible layer and the lower adhesive layer. A third thin hard layer above the adhesive layer could assist in the manufacturing process and channel creation without affecting the adhesive layer.

In one embodiment of the invention, a gradation of rigidity within the first layer could also be employed. For example, the upper surface of the first layer and the lower portion of the first layer could be chemically, mechanically, or thermally treated to be relatively firm. A third thin hard layer would not be necessary.

In another embodiment of the invention, a small, firm but pliable substrate or pad comprising the medical device or catheter management system can lie on a surgical field, separated from, for example, an introducer sheath, vascular access point, or Y-adaptor. The substrate or pad can be attached to the skin or sterile drapes or some other item in the surgical field to maintain its desired position relative to an introducer sheath, vascular access point, or Y-adaptor. The substrate or pad typically has between one and twelve channels, preferably from two to eight or from four to six, channels on it, adapted to hold in place one to twelve associated flexible elongated medical devices or members, with the associated flexible elongated members typically comprising, for example, a guide wire and a catheter. The flexible elongated medical devices or members are said herein to be "associated" with each other because the guide wire and the catheter are used together. The channels can be arranged in a parallel or a curved layout, so as to "fan out" the wire/catheter pairs and to assist in keeping the free ends of each wire/catheter pair separated from the free ends of other pairs. The channels are designed to allow easy insertion and removal of the flexible elongated medical devices or members. Some of the channels can be designed to securely hold a wire or catheter against axial movement, while others can be designed to simply hold a wire or catheter in place relative to the others, without restricting the axial movement of the wire or catheter being held. A series configuration of the pincer units (or channels) can provide additional resistance to the catheter or lead member and prevent translation or rotation of the catheter or member.

The substrate or pad of the medical device or catheter management system has an adhesive surface on its lower side, to allow it to adhere directly to a patient's skin or to a drape or other item to keep it in place on a surgical field, with a selected separation from, and orientation relative to, for example, an introducer sheath, vascular access point, or Y-adaptor. The adhesive surface can be selectively exposed by removing a peel-off cover by pulling off an edge from a protective cover or a tab that extends from said protective cover. It is also within the scope of the invention that instead of an adhesive surface, the bottom portion of the substrate or pad could have VELCRO® hooks, clips, or other functional means to attach the substrate or pad to a desired site on or near a patient.

The substrate or pad can optionally have labels for identifying each wire and each catheter, or each wire/catheter pair. These can be stick-on type labels, or surfaces adapted for writing upon, or they can be pre-molded labeling areas on the pad, with punch-out circles identifying the selected location of each wire/catheter pair. Alternatively, a catheter management system according to the invention may have labels (molded or otherwise) that are part of an injection molded process and reside on the perpendicular prong that presses in on the elongated medical device or member. For example, there may be letters or numbers on the upper surface of the substrate to identify particular elongated medical devices or members.

In another embodiment of the invention, a medical device or catheter management system comprises a flexible substrate for organizing and stabilizing electrophysiology catheters and/or implantable pacemaker and/or defibrillator leads (all termed "wires"). Preferably the system can be sterilized, is disposable, and is inexpensive to manufacture.

In another embodiment of the invention, the system comprises an upper malleable surface with one or more parallel linear channels in which the "wires" can be easily depressed and secured to stabilize the position of said "wires" inside the heart and/or circulatory system. In addition, the "wires" can be easily removed from a channel to freely manipulate said "wires."

In another embodiment of the invention, an upper malleable surface may comprise one or two separate layers. If two separate layers are used, the top upper layer is less malleable and firm to keep the wires contained within, and the lower more malleable material is conformable to the shape of the wire and provides resistance to prevent catheter movement.

In another embodiment of the invention, the system has a lower adhesive surface protected by removable tape to secure said system to a sterile drape or surface.

In another embodiment of the invention, there is an additional firm layer placed above the adhesive layer, which would allow the easy manufacturing and placement of slits in the catheter management system. Slits could easily be cut through an upper surface (firm to malleable) but could stop at a thin hard surface above the adhesive tape.

In another embodiment of the invention, the channels would actually be gaps in which both sides of portions of the upper surfaces do not touch. A space, such as, 20 to 30 mil, may exist to allow easy access an elongated medical device or member into the catheter management system's channels. Without such a gap, it would be more difficult to place elongated medical devices or members directly into the channels. In addition, an additional firm layer provides enough resistance to permit finger pressure over the elongated medical device or member and its entry into the channel. The channel must be wide enough and/or deep enough to receive the catheter, guide wire, sheath, lead, or other elongated medical device or member in whatever shape or size is intended to be received. The sides of the channels may be parallel, or the top of a channel may be wider than the bottom of the channel, or vice versa.

In another embodiment of the invention, the upper surface may not have discrete differences in firmness but rather more gradual differences in firmness.

In another embodiment of the invention, the medical device or catheter management system may include a firm component which could be inserted within a sheath and used to slit biventricular pacemaker, regular pacemaker, and/or defibrillator lead introducer sheaths such that the introducer sheaths themselves could be easily removed while channels of said sheath maintain the lead or leads in their position. Alternatively, the catheter management system could maintain all inserted leads in position and allow slitting of their introducer sheaths and removal of said sheaths using the standard built-in sheath removal embodiments.

In another embodiment of the invention, there is a rigid layer between the patient and a flexible channel layer to ensure that a channel used to hold an elongated medical device or member does not open or release with patient movement or curvature of adhesive surface. The rigid layer would have properties which are stiffer or less malleable than the layer with cut channels.

In another embodiment of the invention, there is a flexible layer between two rigid layers to ensure that a channel used to hold an elongated medical device or member does not open or release with patient movement. The rigid layers would have properties which are stiffer or less malleable than the layer with cut channels.

In another embodiment of the invention, the medical device or catheter management system comprises a flexible layer to face the patient that is cut or shaped to help minimize the effect of the curved surface to which the medical device or catheter management system must adhere. The curved surface would have adhesive on the patient side allowing for the top surface of the catheter management system to remain flat or linear instead of curved during application and preventing the channels from opening and releasing or applying less force to the one or more elongated medical devices or members being held.

In another embodiment of the invention, the medical device or catheter management system has advertising/marketable/instruction material printed on the upside of said system to advertise/market and/or instruct/provide additional information during a procedure. Such information is now between the operator and the patient during the procedure.

In another aspect of the invention, there may be two or more medical device or catheter management systems arranged, for example, in parallel, from about 6 inches to about 3 feet apart, preferably from about 6 to 18 inches apart, to manage and separate two or more catheters, guide wires, sheaths, leads, or other elongated medical devices or members.

In another embodiment of the invention, a sterile, sterilizable, or unsterile disposable multilayered device for managing catheters, guide wires, sheaths, leads, or other elongated medical devices or members comprises:

an upper firm layer having upper and lower surfaces;

a middle compressible foam layer having upper and lower surfaces, the upper surface of the middle compressible layer being attached to the lower surface of the upper firm layer; and a lower adhesive layer for securing said device to or near a patient, which lower adhesive layer has an upper surface that is attached to the lower surface of the middle compressible layer, wherein one or more lateral channels extend inwardly from the upper surface of the upper firm layer through the middle compressible layer to the upper surface of the lower adhesive layer, and wherein one or more catheters, guide wires, leads, sheaths, or other elongated medical devices or members can be positioned in the channels to maintain position relative to each other and then easily be removed.

In another embodiment of the invention, a disposable multilayered device for organizing, holding, and releasing elongated medical devices or members such as catheters, guide wires, leads, and/or sheaths comprises:

an upper firm layer having upper and lower surfaces;

a middle compressible foam layer having upper and lower surfaces, the upper surface of the middle compressible layer being attached to the lower surface of the upper firm layer;

a lower firm layer to provide resistance when pushing an elongated member into said device to secure it; and a lower patient contact adhesive layer for securing said device to or near a patient, which adhesive layer has an upper surface that is attached to the lower surface of the lower firm layer, wherein one or more lateral channels extend from the upper surface of the upper firm layer through the middle compressible layer to the lower firm layer, and wherein one or more elongated medical devices or members can be positioned in the channels to maintain position and then easily be removed.

In another embodiment of the invention, an elongated medical device or member is secured by pushing down on both sides of the channels and releasing. Removal is achieved by pulling up on the elongated medical device or member.

In another embodiment of the invention, an elongated medical device or member is secured in place by pushing down on the groove and pulling up to release the elongated medical device or member.

In another embodiment of the invention, the channels are substantially parallel to each other.

In another embodiment of the invention, the channels form a fan configuration as viewed from above.

In another embodiment of the invention, the device comprises a firm layer between the middle compressible layer and the lower adhesive layer.

In another embodiment of the invention, the upper surface of the upper firm layer is capable of displaying indicia.

In another embodiment of the invention, the channels may be the same size or variable in size to accommodate a variety of elongated medical devices or members of different widths.

In another embodiment of the invention, two or more medical device or catheter management systems are organized adjacent to one another (and separated by a comfortable working distance of from about 0.5 to about 6 inches) but perpendicular to the elongated medical devices or members to organize the elongated members and/or their connector cables and prevent entanglement of said members.

In another embodiment of the invention, two or more catheter management systems are organized parallel to one another (and separated by from about 0.5 to about 3 feet) but perpendicular to the elongated medical devices or members to organize the elongated medical devices or members and/or their connector cables and prevent entanglement of said members.

In another embodiment of the invention, a labeling system is also provided (within or on) to help identify each elongated medical device or member.

In another embodiment of the invention, a disposable multilayered device for managing elongated medical devices or members comprises:

an upper component having upper and lower surfaces, wherein one or more lateral channels extend from the upper surface of the upper component into the upper component; and a lower component capable of releasably attaching to a desired location on or near a patient, wherein one or more elongated medical devices or members can be positioned in the channels to maintain position relative to each other and then easily be removed.

In another embodiment of the invention, a sterile, sterilizable, or unsterile disposable multilayered device for managing elongated medical devices or members comprises:

a first layer having upper and lower surfaces and having one or more lateral channels extending therethrough;

a second layer positioned beneath the first layer and having upper and lower surfaces;

a third, firm layer having a top surfaced affixed to the lower surface of the second layer and a lower surface; and a fourth layer having an upper surface attached to the lower surface of the third layer and a lower adhesive surface for securing said device to or near a patient, wherein the upper layer of the first layer is firmer than the rest of the first layer, and wherein one or more elongated medical devices or members can be positioned in the channels to maintain position relative to each other and then easily be removed.

In another embodiment of the invention, the first layer and the second layer together comprise a continuous component.

In another embodiment of the invention, a medical device or catheter management system is fabricated in a manner as to create a structure with a variety of layers of different quantifiable properties related to hardness, bendable, flexibility, tensile strength, and/or stress and strain. The combination of these properties creates a system in which at least one elongated member and/or medical device can be pushed into a channel, slot, slit, or gap such that the system contains at least one layer that is more flexible to absorb, conform to, and grip said medical device and/or elongated member and another layer that is less flexible (i.e., harder) to provide resistance when pushing the at least one medical device and/or elongated member into the slit, slot, channel, or gap of the catheter management system. This embodiment also would have an attached bottom layer such that the catheter management system could easily adhere or attach to a patient, sterile drape, and/or other support system or table on or around a patient.

In another embodiment of the invention, one layer or at least one of the layers in a unit is a substrate comprised of an upper continuous component, with the addition of an adhesive layer or structure on the bottom. The upper continuous component is formed by a process, which creates a single biomaterial a continuous component identifiable by a variety of stress and strain properties, flexibility, resilience, hardness, or any other characteristic determining the ability of said structure to bend, or move under a force. Said continuous component could be comprised of a polymer, copolymer, plastic or rubber, thermoplastic, composite material, admixture, polymeric matrix, crystalline structure, polyethylene/polyacetate/polycarbone/polychloroprene/ glass/carbon/graphite/silicone/boron/ceramic/organic fibers or a combination thereof. It is also understood that the continuous component could be fabricated in a variety of manners.

In another embodiment of the invention, a unit for managing one or more elongated medical devices or members, comprises:

a substrate having one or more channels each extending from a first surface to a second opposed surface, wherein each channel has a depth sufficient to receive an elongated medical device or member and the channel comprises one or more protrusions, substances, or both capable of releasably holding the elongated medical device or member.

In another embodiment of the invention, a unit for managing one or more elongated medical devices or members, comprises:

a substrate having one or more channels each extending from a first lateral surface to a second opposed lateral surface, wherein each channel has a depth sufficient to receive an elongated medical device or member and the channel comprises one or more protrusions, substances, or both capable of releasably holding the elongated medical device or member.

In another embodiment of the invention, the substrate is flexible.

In another embodiment of the invention, the substrate has two or more channels.

In another embodiment of the invention, each channel has at least two protrusions that alternatingly extend in opposite directions. At least one channel is curvilinear.

In another embodiment of the invention, the substrate has a flat or substantially flat bottom surface and one or more adhesive layers are attached to the bottom surface.

In another embodiment of the invention, the substrate is slightly curved in a longitudinal direction.

In another embodiment of the invention, a device for managing one or more medical devices comprises an elongated flexible substrate having one or more channels each extending from a first lateral surface to a second opposed lateral surface, wherein each channel has a depth sufficient to receive an elongated medical device and the channel is sufficiently curvilinear to be capable of releasably holding the elongated medical device. The device may have a single channel, two channels, or as many as six or eight channels.

In another embodiment of the invention, each channel comprises at least one protrusion that extends from about 10 to about 90%, preferably from about 15 to about 80%, more preferably from about 20 to about 60% perpendicularly across the channel.

In another embodiment of the invention, each channel has at least two protrusions that alternatingly extend in opposite directions.

In another embodiment of the invention, the substrate has a flat or substantially flat bottom surface and one or more adhesive layers are attached to the bottom surface.

In another embodiment of the invention, an elongated medical device or member is secured in place by pushing down on the elongated medical device or member in the channel, and the elongated medical device or member is removed by pulling up to release it. In addition, placement in the channel may be non-linear in that the elongated medical device or member will be draped or positioned in a curvilinear manner around a curvilinear tract formed by a centrally placed prong (or perpendicular resistive component).

In another embodiment of the invention, an assembly comprises two or more units, each unit comprising a substrate having one or more channels each extending from a first surface to a second opposed surface, wherein each channel has a depth sufficient to receive an elongated medical device and each channel comprises one or more protrusions, substances, or both capable of releasably holding the elongated medical device or member, wherein more than one elongated medical device or member is organized parallel to one another, and separated but perpendicular to the elongated medical devices or members to organize the elongated medical devices or members and/or their connector cables and prevent entanglement of said elongated medical devices or members.

In another embodiment of the invention, an assembly comprises two or more units, each unit comprising a substrate having one or more channels each extending from a first lateral surface to a second opposed lateral surface, wherein each channel has a depth sufficient to receive an elongated medical device or member and the channel comprises one or more protrusions, substances, or both capable of releasably holding the elongated medical device or member, wherein more than one elongated medical device or member is organized parallel to one another, and separated but perpendicular to the elongated medical devices or members to organize the elongated medical devices or members and/or their connector cables and prevent entanglement of said elongated medical devices or members.

In another embodiment of the invention, a labeling, lettering, or numbering system is also provided to help identify each elongated medical device or member.

In another embodiment of the invention, the unit may have a slight bend in the longitudinal direction that flattens out when the device is placed on a flat or plane surface.

In another embodiment of the invention, an assembly or module for releasably holding at least one elongated medical device or member, comprises two or more holding units each having a substrate with a channel extending from a first lateral surface to a second opposed lateral surface, wherein the channels are aligned and each channel has a depth sufficient to receive the elongated medical device or member and each channel comprises one or more protrusions, substances, or both capable of releasably holding the elongated medical device or member. The channels may be linear, but preferably they are nonlinear or curvilinear.

In another embodiment of the invention, an assembly or module comprises 2 to 4 substrates. The design of each substrate is such that the entry and exit points for each elongated medical device or member are parallel to one another, though the channels may be nonlinear or curvilinear.

In another embodiment of the invention, two or more substrates comprise a continuous member.

In another embodiment of the invention, an assembly or module comprises holding units that are permanently or releasably attached to one another.

In another embodiment of the invention, a sterile medical unit for holding and releasing elongated medical devices or members, comprises;

an upper flexible substrate comprising at least one curvilinear channel with at least one perpendicular resistance component and a lower, adhesive surface, wherein the rotation and translation of the elongated medical devices or members can be controlled and the elongated medical devices or members can be easily removed for additional manipulation.

In another embodiment of the invention, the elongated medical devices or members may be of different sizes.

In another embodiment of the invention, the elongated medical devices or members are selected from the group consisting of catheters, leads, guide wires, wires, devices, or medical tubing of some sort.

In another embodiment of the invention, the depth and width of each linear, nonlinear, or curvilinear channel is sufficient to receive and hold an elongated medical device or member.

In another embodiment of the invention, a perpendicular resistance component is centrally located towards the concavity of the channel to provide sufficient resistance to prevent rotation and translation of each elongated medical device or member.

In another embodiment of the invention, the device has two or more curvilinear channels aligned in parallel to hold and release multiple elongated medical devices or members.

In another embodiment of the invention, an assembly comprises two or more holding units arranged in parallel or in series, or in a combination thereof.

In another embodiment of the invention, an assembly comprises two or more curvilinear channels aligned in series to augment and enhance the resistant to said elongated medical device or member to further prevent rotation and translation of said elongated medical device or member.

In another embodiment of the invention, in an assembly two or more holding units have lateral surfaces that can be permanently or releasably adjoined to hold the units in place adjacent to each other.

In another embodiment of the invention, a device for managing one or more elongated medical devices or members, comprises:

a flexible substrate having one or more curvilinear channels each extending from a first lateral surface to a second opposed lateral surface, wherein the substrate has a flat or substantially flat bottom surface and one or more adhesive layers are attached to the bottom surface, and wherein each channel has a depth sufficient to receive an elongated medical device or member and the channel comprises one or more protrusions, substances, or both capable of releasably holding the elongated medical device or member.

In another embodiment of the invention, a substrate has two or more channels.

In another embodiment of the invention, each channel comprises at least one protrusion that extends from about 20 to about 60% perpendicularly across a channel.

In another embodiment of the invention, each channel has at least two protrusions that alternatingly extend in opposite directions.

In another embodiment of the invention, the substrate is slightly curved.

In another embodiment of the invention, the substrate is elongated.

In another embodiment of the invention, a device for managing one or more elongated medical devices or members, comprises:

an elongated flexible substrate having one or more channels each extending from a first surface to a second opposed surface, wherein each channel has a depth sufficient to receive an elongated medical device or member and the channel is sufficiently curvilinear to be capable of releasably holding the elongated medical device or member and wherein the substrate has a flat or substantially flat bottom surface and one or more adhesive layers are attached to the bottom surface.

In another embodiment of the invention, the one or more channels extend from a first lateral surface to a second opposed lateral surface.

In another embodiment of the invention, each channel comprises at least one protrusion that extends from about 10 to about 90% perpendicularly across a channel.

In another embodiment of the invention, each channel comprises at least one protrusion that extends from about 15 to about 80% perpendicularly across a channel.

In another embodiment of the invention, each channel comprises at least one protrusion that extends from about 20 to about 60% perpendicularly across a channel.

In another embodiment of the invention, each channel has at least two protrusions that alternatingly extend in opposite directions.

In another embodiment of the invention, the substrate is slightly curved.

In another embodiment of the invention, an elongated medical device or member is secured in place by pushing down on the channel or the elongated medical device or member, and the elongated medical device or member is removed by pulling up to release it.

In another embodiment of the invention, an elongated medical device or member is secured in place by wrapping the device or member around the protrusion and pushing down. Alternatively, by pulling up on the device or member, it may be released.

In another embodiment of the invention, the substrate has an upper surface capable of displaying indicia. For example, letters can be imprinted or formed on top of the resistive protrusion in a curvilinear channel to help organize elongated medical devices or members.

In another embodiment of the invention, the channels may be the same size or variable in size to accommodate a variety of the elongated medical devices or members of different widths.

In a preferred embodiment of the invention, three or more curvilinear channels molded into a rubber like substance are aligned in a single system, each channel with a labeled centrally placed resistive protrusion to hold three or more elongated medical devices or members. The bottom surface is comprised of sterile biocompatible adhesive (covered by removable tape). The entire system is sterile, and compatible for placement on the skin or sterile drapes proximal to insertion of elongated medical devices or members.

In another embodiment of the invention, in an assembly of two or more catheter management devices, more than one elongated medical device or member is organized parallel to one another, and separated but perpendicular to the elongated medical devices or members to organize the elongated medical devices or members and/or their connector cables and prevent entanglement of said elongated medical devices or members.

The novel features of this invention, as well as the invention itself, will be best understood from the attached drawings, taken along with the following description, in which similar reference characters refer to similar parts.

BRIEF DESCRIPTION OF THE DRAWINGS

FIG. 7D represents a medical holding unit comprising a substrate with an attached adhesive layer;

FIGS. 12A and 12B are top and lateral views, respectively, of an embodiment of the invention suitable to having an attached splitter assembly.

DETAILED DESCRIPTION OF THE INVENTION

Figure 1:
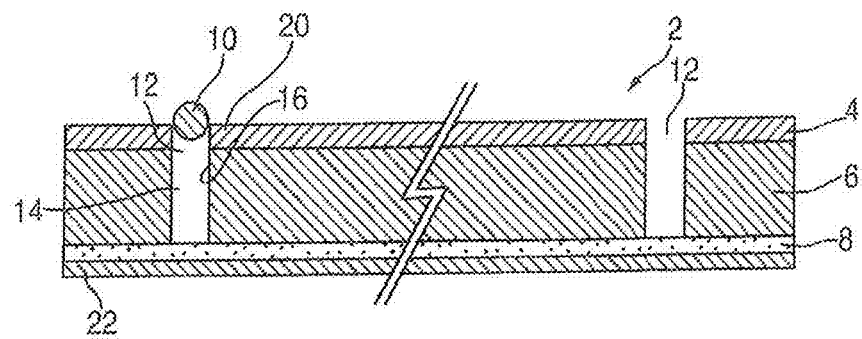
FIG. 1 is a schematic cross-sectional representation of an embodiment of the invention.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced. It should be understood that the invention is not necessarily limited in its application to the details of construction and the arrangement of the components and/or methods set forth in the following description and/or illustrated in the drawings. The invention is capable of other embodiments or of being practiced or carried out in various ways.

As shown in FIG. 1, a section 2 of a medical device or catheter management system according to the invention comprises a firmer upper surface or layer 4, a less firm middle layer 6, and a non-allergenic adhesive layer 8 comprising a substrate. A "wire" 10, such as a catheter, guide wire, lead, sheath, or other elongated medical device or member, is positioned at the opening or entrance 12 to a lateral groove, slit, slot, gap, or other opening, i.e., channel, 14 having inner surfaces 16. When the operator (not shown) presses downward on wire 10, upper surface sections 20 of layer 4 bend downward so that the middle layer 6 on each side of channel 14 is compressed. Then, wire 10 moves downward below sections 20, sections 20 recoil upward, and inner surfaces 16 compress wire 10, trapping wire 10. Surfaces 16 and middle layer 6 provide resistance, that is, they prevent movement while upper layer 4 holds wire 10 in. Catheter management system 2 as well as the other embodiments shown and described herein will preferably have a removable polymeric layer 22 covering the bottom of adhesive layer 8.

Figure 2:
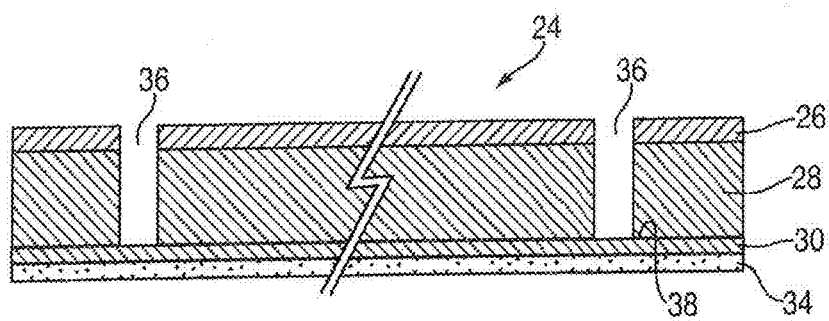
FIG. 2 is a schematic cross-sectional representation of another embodiment of the invention.

Removal of wire 10 is easy. From the side the operator applies upward pressure to wire 10 so that it is pushed up from section 2 and released for manipulation In the embodiment of the invention shown in FIG. 2, a medical device or catheter management system 24 comprises a firmer upper surface or layer 26, a less firm middle layer 28, a lower layer 30, and a non-allergenic adhesive layer 34. Lateral grooves, slits, slots, or gaps or other openings, i.e., channels, 36 extend from upper layer 26 to the upper surface 38 of lower layer 30.

Figure 3:
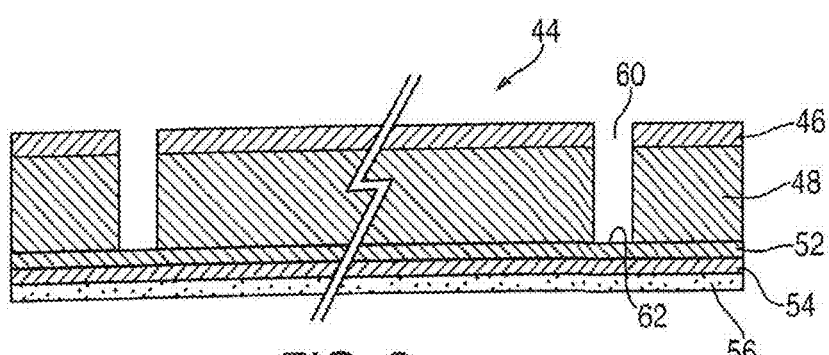
FIG. 3 is a schematic cross-sectional representation of a further embodiment of the invention.

In the embodiment of the invention shown in FIG. 3, a medical device or catheter management system 44 comprises a firmer upper layer or surface 46, a less firm middle layer 48, a rigid layer 52, optionally a lower layer 54, and an adhesive layer 56. Lateral grooves, slits, slots, gaps, or other openings, i.e., channels, 60 extend from upper layer 46 to an upper surface 62 of rigid layer 52.

Figure 4:
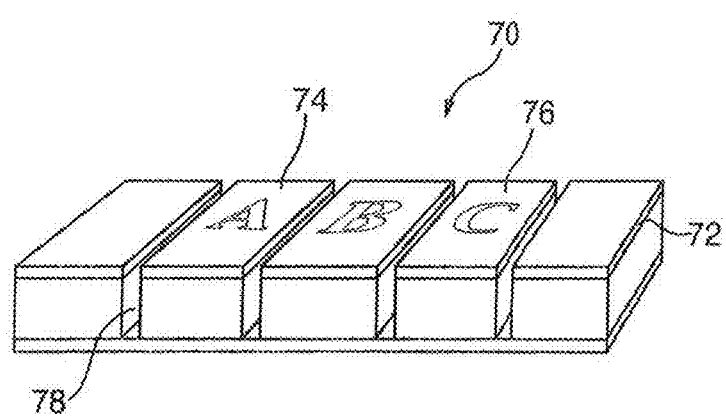
FIG. 4 is a schematic oblique representation of an embodiment of the invention.

In FIG. 4, a medical device or catheter management system 70 has an upper layer 72 with an upper surface 74 upon which printing or other indicia 76, such as instructions, a warning, or a company name or logo, or any combination thereof, could appear. Whereas the grooves, slits, slots, gaps, or other openings, i.e., channels, 78 might normally be spaced uniformly across upper surface 74, optionally channels 78 may be positioned so that there is a larger upper surface for such indicia. Also, two or more of channels 78 may be parallel or non-parallel. For example, channels 78 may be arranged in a fan shape.

Figure 5:
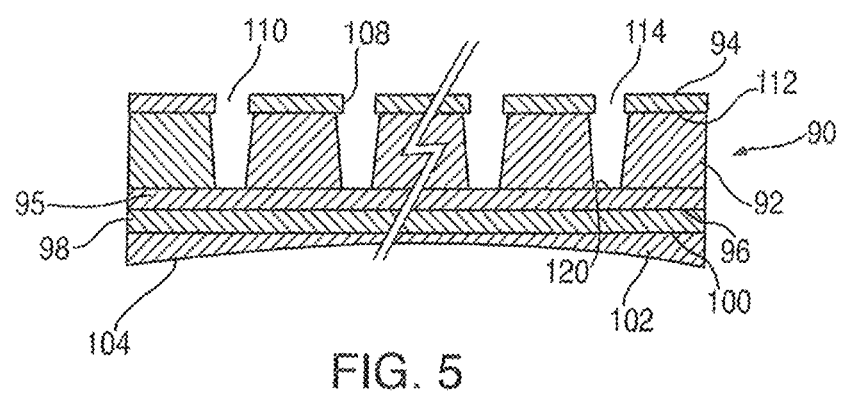
FIGS. 5 and 6 are each a schematic cross-sectional representation of another embodiment of the invention.
Figure 6:
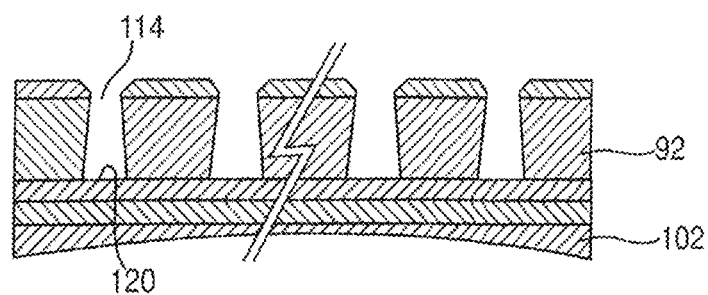

The medical device or catheter management systems set forth in FIGS. 5 and 6 represent additional embodiments of the invention. In FIG. 5, a system 90 has a first layer 92 with an attached upper layer or surface 94 comprised of material firmer than the material of first layer 92. First layer 92 is attached to second layer 95, which is in turn attached at boundary 96 to a firmer third layer 98. The lower surface of third layer 98 is attached at boundary 100 to a fourth, adhesive layer 102. Adhesive layer 102 has a surface 104, preferably curved, that comprises adhesive or other chemical or mechanical means for bonding with a patient's skin or clothing or with a drape or other flexible or hard surface in an operating room or medical facility (not shown).

Upper layer or surface 94 can be coextensive with the upper boundary 112 of first layer 92 or the lateral edges 108 of upper layer or surface 94 can extend into a channel 110 as shown in FIG. 5 or be withdrawn or recessed from channel 110 as shown in FIG. 6.

As can be seen, channel 110 can be wider at its top 114 than at its bottom 120, as in FIG. 5, or narrower at its top 114 than at its bottom 120, as in FIG. 6. Optionally, as shown in other embodiments, the sides of channel 110 can be substantially parallel.

Although first layer 92 and second layer 95 are depicted as two separate components, it is within the scope of the invention that first layer 92 and second layer 95 can form a single continuous unit, element, or component of the same material.

Overall the medical device or catheter management systems of the invention described above comprise firm but flexible material. Upper layers 4, 26, 46, 72, and 94 and rigid layers 52 and 98 comprise a rigid or semi-rigid polymeric material such as a polycarbonate. Useful polymeric materials include, but are not limited to, LEXAN® polycarbonate materials available from GE Plastics.

Middle layers 6, 28, 48, and 95 comprise a less rigid, more resilient polymeric material such as a polyacetate, polycarbonate, or polyethylene foam. Useful polymeric foams include, but are not limited to, ethylene vinyl acetate and many of the polychloroprene synthetic rubbers available as Neoprene from DuPont. Lower layers 30 and 54 preferably comprise a polymeric material that is less resilient than the middle layer, such as a polycarbonate. Useful polymeric materials for this layer include, but are not limited to, LEXAN® polycarbonate materials.

Adhesive layers 8, 34, 56, and 102 comprise pre-formed adhesive tape that is sticky on both the upper and lower surfaces and has peel away protective tape on both surfaces. One surface is exposed when the catheter management system is assembled; the other surface is exposed when the catheter management system is applied to a desired surface. Examples of adhesive tapes or substrates that are useful include 3M's 1587 and 1772 contact adhesives, which have a 1/16" polyethylene foam substrate. Alternatively, direct adhesive could be applied to the bottom surface with protective peel off tape with a tab to provide easy removal.

Individual layers are bound together by an appropriate medical grade adhesive. 3M's 1510 acrylic adhesive has been useful in this regard. In addition, individual layers can be adhered together by heat or other chemical or mechanical means.

Optionally the medical device or catheter management system could have two or more flat tabs to provide surfaces to which surgical clamps can be attached, to hold the pad, for example, on a surgical drape. In addition, the bottom adherent surface could be a VELCRO® component or clip.

With regard to grooves, slots, gaps, slits, channels, or other openings in the upper surface of the catheter management system, a groove, slot, gap, slit, channel, or other opening can be pushed open, and a catheter, guide wire, sheath, lead, or other elongated medical device or member can be inserted laterally into the groove, slot, gap, slit, channel, or other opening, which will then close back around the catheter, guide wire, sheath, lead, or other elongated medical device or member and hold it in place, to prevent movement in the transverse or axial direction.

The depths of the various layers can vary according to the application and materials. Typically the upper layers 4, 26, 46, 72, and 94 will each be from about 0.3 mm to about 0.7 mm thick, and the middle layers 6, 28, 48, and 92 will each be from about 0.1 cm to about 0.5 cm thick. Lower layers 30, 54, and 95 will each be from about 0.1 cm to about 0.3 cm thick, and adhesive layers 8, 34, 56, and 102 will each be about 0.1 cm to about 2.5 cm thick. Channels 14, 36, 60, and 110 can be from about 0 mils (a slit) to about 30 mils wide, preferably from about 20 to about 30 mils wide (what are termed gaps). Channels 14, 36, 60, and 110 are preferably from about 1.5 cm to about 2.0 cm apart, but this can vary, according to the operator's wishes, habits, or desires. Additional sizes and dimensions could be configured for microsurgical applications as well as macrosurgery.

The grooves, slits, slots, gaps, channels, or openings can vary in shape and size to accommodate catheters, guide wires, leads, sheaths, or other medical devices or members, which have different diameters. However, thin slits in the above design can accommodate a variety of elongated medical device or member sizes and shapes due to the material engineering design (firm but malleable upper layer and softer lower layer or some variation thereof).

The dimensions of the medical device or catheter management system described above can vary greatly due to the intended application and the number of "wires" that may be used. In one embodiment of the invention, the substrate may have a length of from about 0.5 to about 10.0 inches, a width of from about 0.2 to about 5.0 inches, and a thickness of from about 0.1 to about 0.5 inches.

It is within the scope of the invention that a medical device or catheter management system, that is, a sterile disposable multilayered device for managing catheters, guide wires, leads, sheaths, or other medical devices, can be more simply viewed as a two component system. As a first component, an upper component has upper and lower surfaces, wherein one or more lateral grooves, slots, channels, or gaps extend from the upper surface of the upper component into the upper component. The second component comprises means of, attaching, optionally releasably attaching, to a desired location on or near a patient. One or more catheters, guide wires, leads, sheaths, or other medical devices or members can be positioned in the grooves, slots, or gaps to maintain position relative to each other and then easily be removed.

The first component may comprise the one or more layers described above, where the first component may have firm, soft, and then firm layers, or firm, soft, soft, and firm layers. Moreover, whereas there may two adjacent layers that could be the same material, there may in fact only be one layer, for example, one where the gaps, grooves, or slots do not go through the entire combined layer but only to a depth consistent with what may have been the first upper layer.

In another embodiment of the invention, a sterile resistive medical holding unit is capable of holding and releasing at least one elongated medical device or member. The medical holding unit comprises an upper flexible substrate comprising at least one channel with at least one resistive component and a lower adhesive surface or layer. The rotation and/or translation of each elongated medical device or member can be controlled, and each elongated medical device or member can be easily removed from the medical holding unit when sufficient force is manually applied to the elongated medical device or member to release the elongated medical device or member from the medical holding unit for additional manipulation.

The depth and width of each channel is sufficient to receive and hold an elongated medical device or member. The resistive component characteristic of a channel that holds an elongated medical device or member can be mechanical, such as a particular configuration, or chemical, such as a mild adhesive or other tacky substance. For example, a channel could be nonlinear or curvilinear with one or more protrusions or curves that provide a force perpendicular to the longitudinal axis of the elongated medical device or member, to cause the elongated medical device or member to fit snugly in the channel. The perpendicular resistive component provides resistance to rotation or translation, or both, of the elongated medical device or member. The channels may have variable widths, depths, and locations of the perpendicular resistance components to control the resistance of a variety of elongated medical devices or members based upon their particular size. For example, a channel may have one or more protrusions that each extend perpendicularly from about 10 to about 90%, preferably from about 15 to about 80%, more preferably from about 20 to about 60%, across the width of a channel.

Each holding unit may comprise one or more linear, nonlinear, or curvilinear channels, each with at least one perpendicular resistance force component. The channel cross-sections may be rectangular, rounded, square, triangular, or any shape that permits entry and release of an elongated medical device or member. Preferably the cross-sections are substantially similar within the holding unit, but they may vary. The perpendicular resistance force components must work by holding the elongated medical devices or members without deforming them or impairing their functionality, such as, for example, by kinking or otherwise impairing the flow of liquid. The perpendicular resistance force components do not need to be one to a channel but could be more than one or may even be a lip on a channel. They do not need to be perpendicular in direction or shape, they only need to impart a significant force equal to and opposite that of any rotational or translational force that may be applied to the elongated member when they are intended to be held in place. When an active perpendicular resistance force component is applied to the elongated medical device or member in these holding units, it must exceed and overcome this passive perpendicular resistance force component to release it from the channel. The perpendicular resistance force components could be balls, cylinders or rods, boxes, or any such shape that imparts a force to the elongated medical device or member and prevents rotation or translation of the elongated member once in the channel. The degree of channel impingement, as well as the perpendicular resistance force components own flexibility, may be important features in this.

A multiple elongated member holding, or holding and releasing, assembly or module is defined as a collection of, that is, two or more, medical holding units such that when they are aligned perpendicular to, or in the direction of, the direction of at least one elongated medical device or member they can handle more than one elongated medical device or member simultaneously An augmented elongated medical device or member holding unit is defined as two or more holding units arranged so that units with essentially coextensive channels attach serially to an elongated medical device or member to amplify the holding properties above and beyond a single holding unit.

A medical holding unit according to the invention may comprise one or more channels and may be used by itself or spaced apart from another medical holding unit. It is within the scope of the invention that two or more medical holding units may be permanently or releasably attached to one another for use in desired situations. For example, two medical holding units each having a single channel or more than one channel could be attached to each other so that the channels are coextensive and an elongated medical device or member would extend from one channel immediately into another channel in the other holding unit. Such an arrangement would provide increased holding force to hold an elongated medical device or member in position. Alternatively, a medical holding unit having two parallel channels may be attached to a medical holding unit having only one channel that would then be coextensive with only one channel of the first medical holding unit. Similarly, medical holding units having the same or different numbers of channels can be assembled in whatever combination is necessary for the one or more elongated medical device or member being held.

It is within the scope of the invention that the medical holding units can be permanently or releasably attached to one another. For example, the medical holding units could be glued together in a desired configuration with a conventional medical grade adhesive, or lateral surfaces to the medical holding units could have adhesive patches covered by removable strips. In another embodiment, the medical holding units may have physical structure such as protrusions and reciprocal receiving structure such as slots so that the medical holding units can be assembled as desired, similar to LEGO building blocks or other instances where holding units can be snapped or locked together. Other physical attachment useful here would include VELCRO® materials or any other snaps, hooks, or the like that would hold the holding units together.

Figures 7A, 7C:
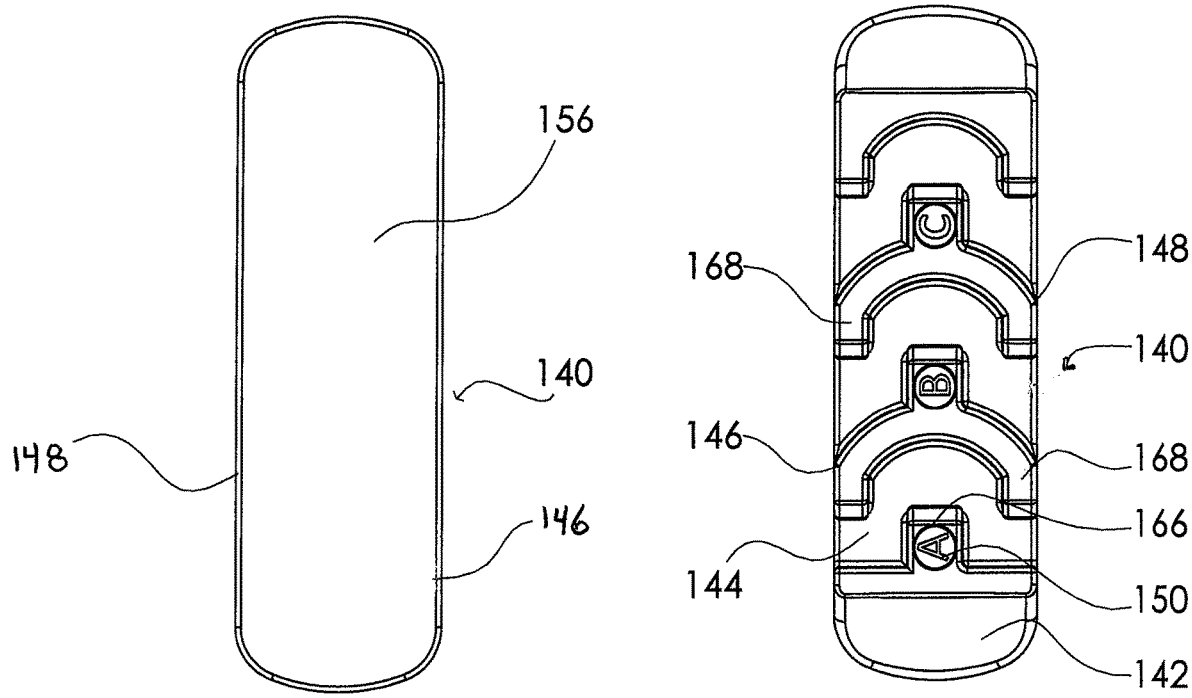
FIGS. 7A-7D are schematic representations of another embodiment of the invention, where
Figure 7B:
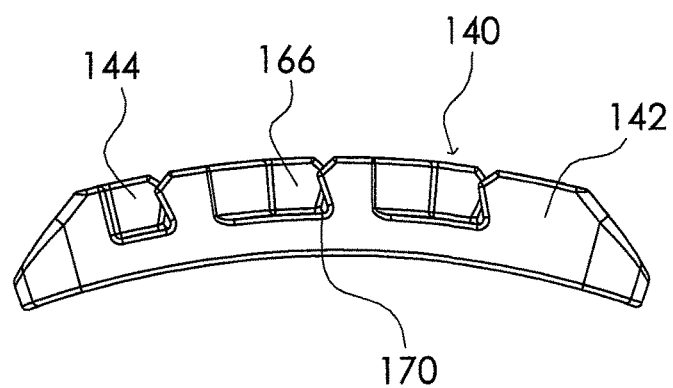
Figure 8:
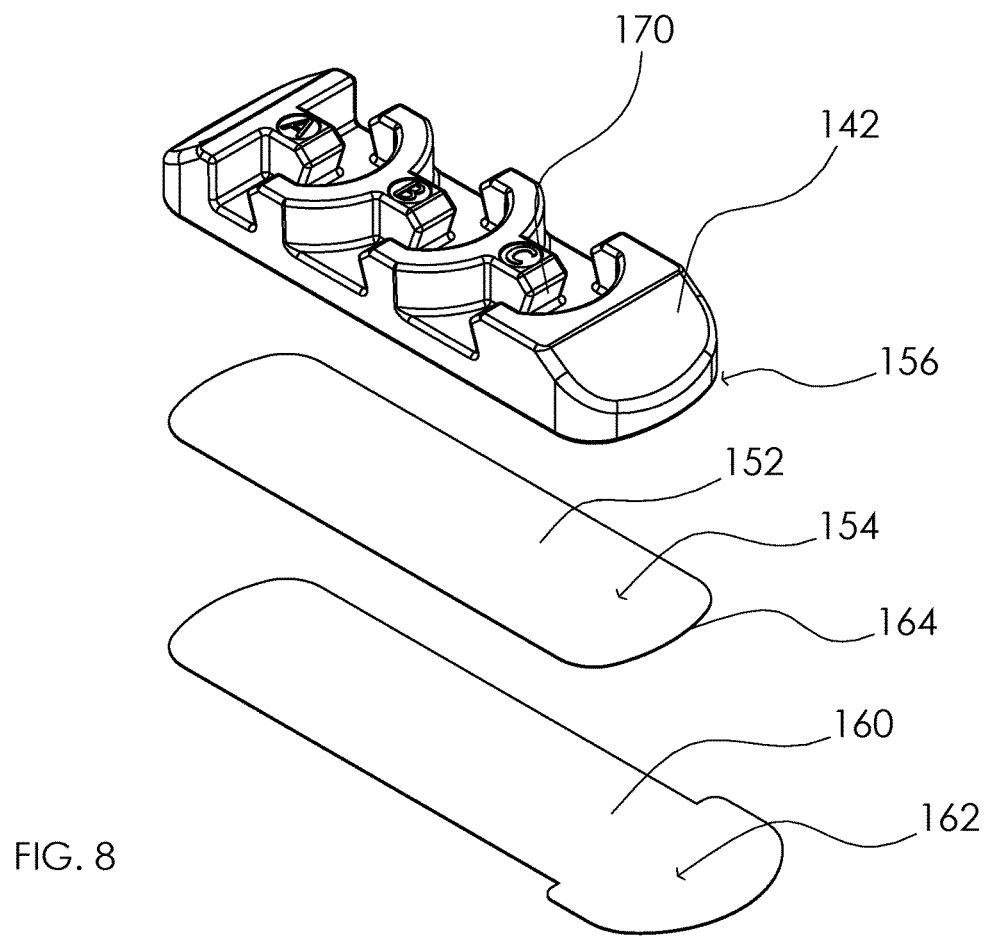
FIG. 8 is a schematic representation of the embodiment shown in FIG. 7D where the components are separated.

In the embodiment of the invention shown in FIGS. 7A to 8, a medical holding unit 140 comprises a substrate 142 with one or more grooves or channels 144. Each channel 144 extends from one lateral side 146 to another opposed lateral side 148 and has a depth and width sufficient to receive an elongated flexible medical device (not shown).

Figure 7D:
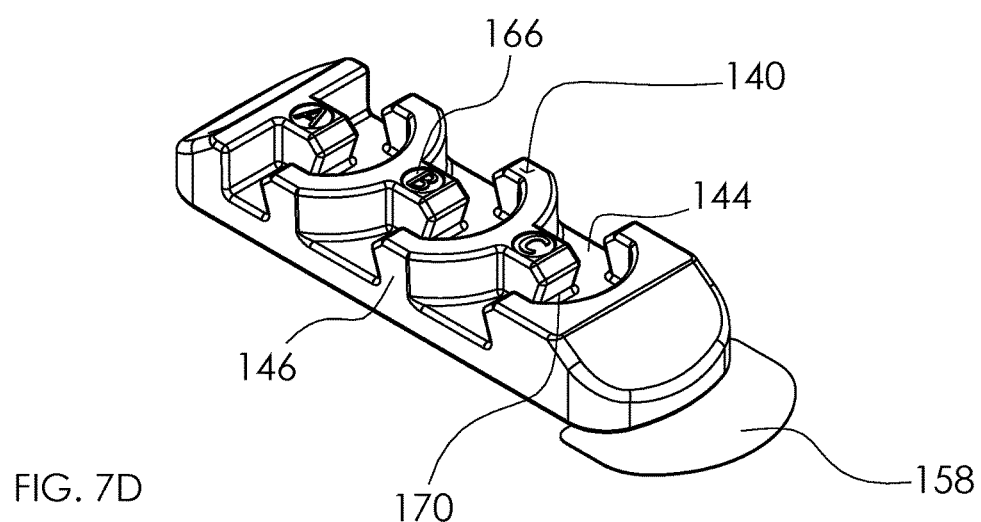

An upper surface 152 of an adhesive layer 154 adheres to a bottom surface 156 of substrate 142. An upper surface 160 of a removable flexible substrate 162 adheres to a bottom surface 164 of adhesive layer 154. Adhesive layer 154 may form a tab 158, as shown in FIG. 7D.

Each channel 144 is dimensioned and/or configured to be capable of releasably holding an elongated medical device or member (not shown). In FIGS. 7A, 7B, 7D, and 8, each channel 144 has at least one protrusion 166 that is capable of engaging an elongated medical device or member (not shown) to releasably hold it, where the channel is also defined by formed ridge 168. Alternatively, there could be two or more protrusions 166 extending alternatingly in opposite directions or another physical arrangement to releasably hold an elongated medical device or member. Optionally, protrusions 166 may have letters or numbers 150 to identify a channel for a particular elongated medical device or member (not shown). In another embodiment of the invention, a channel 144 could comprise a tacky substance alone or in combination with one or more protrusions.

Preferably channels 144 are substantially uniform in cross-section from one lateral side to the opposed other lateral side for a particular channel, although each channel 144 on a substrate 142 does not necessarily have the same depth or cross-section or longitudinal shape.

Figure 9:
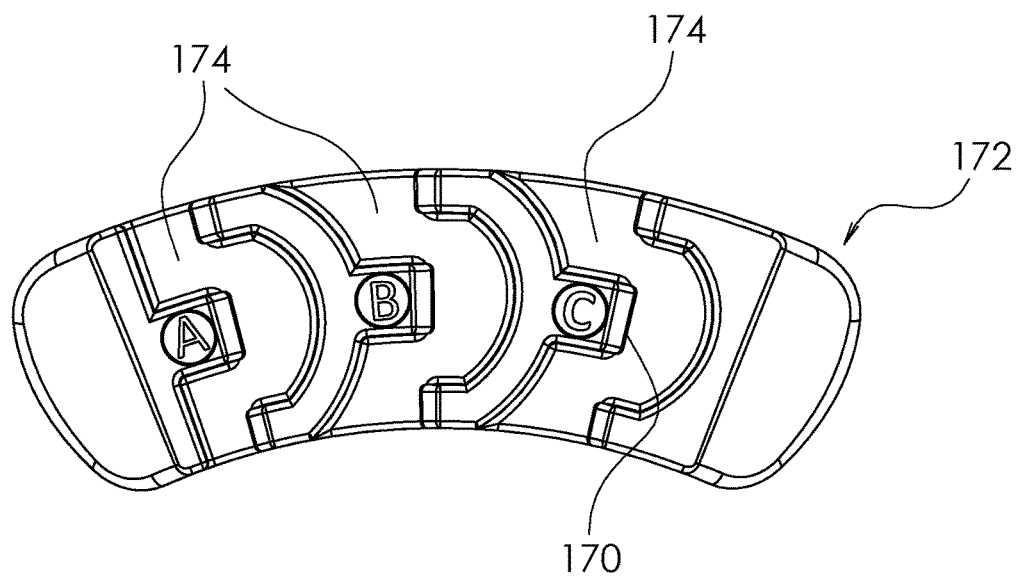
FIG. 9 is a schematic representation of an embodiment of the invention where the grooves or channels are in a "fan shape"

As shown in the lateral view of FIG. 7B, substrate 142 optionally may be slightly curved to better fit on a curved surface, such as a patient's leg, arm, or torso. Since substrate 142 is comprised of a flexible material, it will also fit a flat or substantially flat surface In another aspect of the invention, as set forth in FIG. 9, a medical holding unit 172 may be slightly curved and the grooves or channels 174 may be in a "fan shape." Each channel 174 has a projection 170.

Figure 10A:
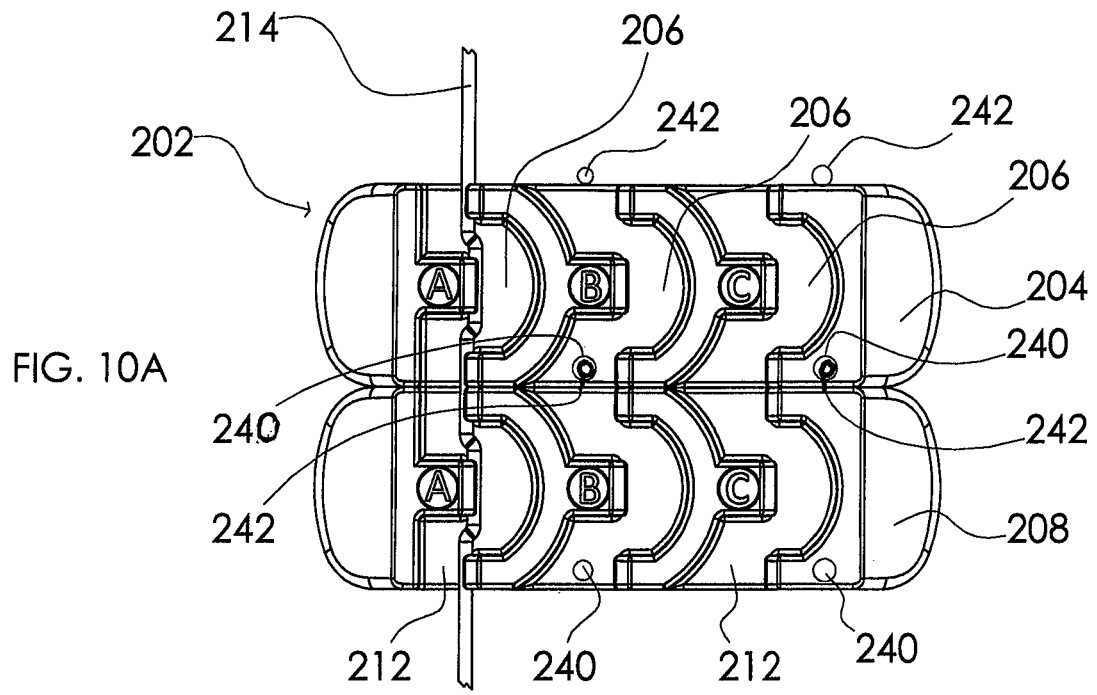
FIGS. 10A to 10D are schematic representations of assemblies or modules according to the invention having two or more medical holding units.

In another embodiment of the invention, a catheter management assembly or module 202 shown in FIG. 10A may comprise a medical holding unit 204 with channels 206 and a medical holding unit 208 with channels 212, to substantially increase the rotational and translational holding ability, for example, with regard to holding catheter 214. Medical holding units 204 and 208 may be separate members that are permanently or removably affixed to one another by glue or mechanical means or they may be manufactured as one continuous unit. For example, medical holding unit 208 has openings 240 to receive projections 242, as shown on medical holding unit 204.

Figure 10B:
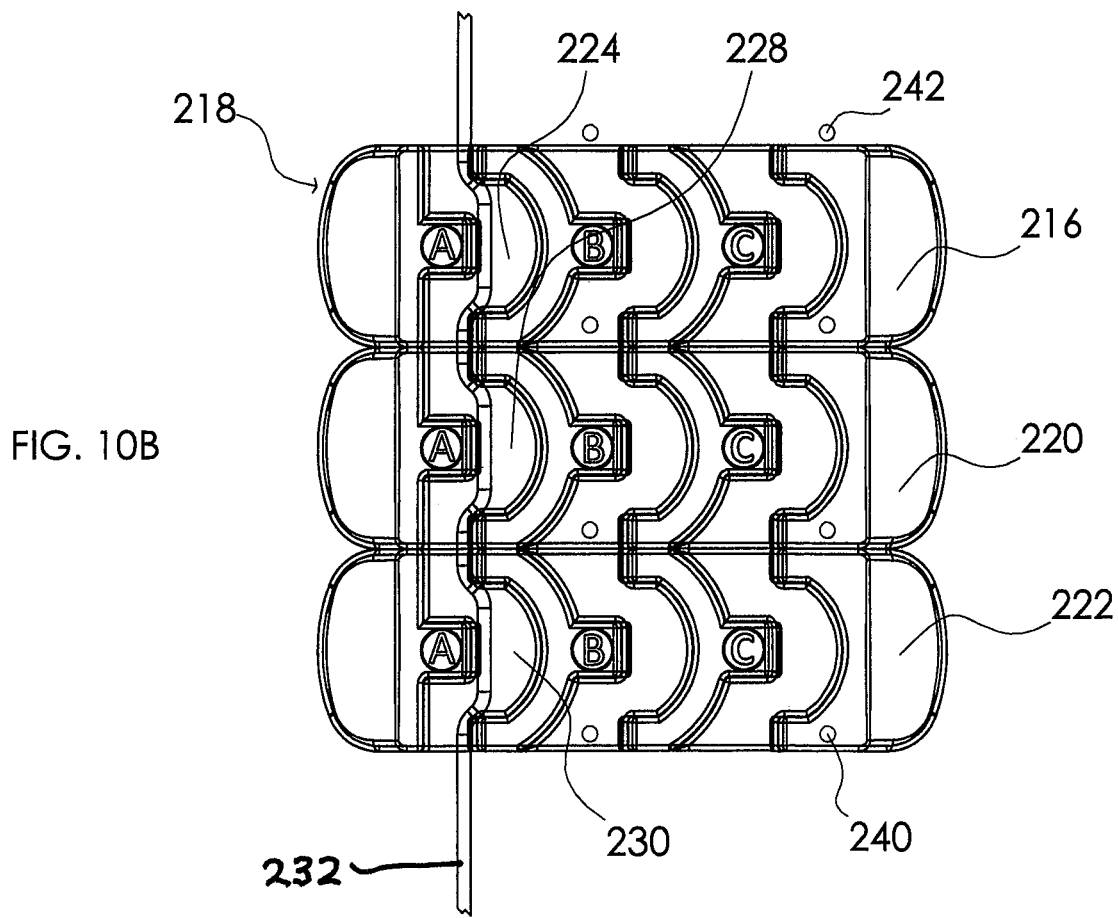

Each medical holding unit may have more than one channel, and assembly or module 202 may comprise more than two medical holding units, as shown in assembly 218 in FIG. 10B. Medical holding units 216, 220, and 222 have channels 224, 228, and 230, respectively, to hold a catheter 232. It is within the scope of the invention that different medical holding units having different numbers of channels may be attached to one another to form an assembly or module.

Figure 10C:
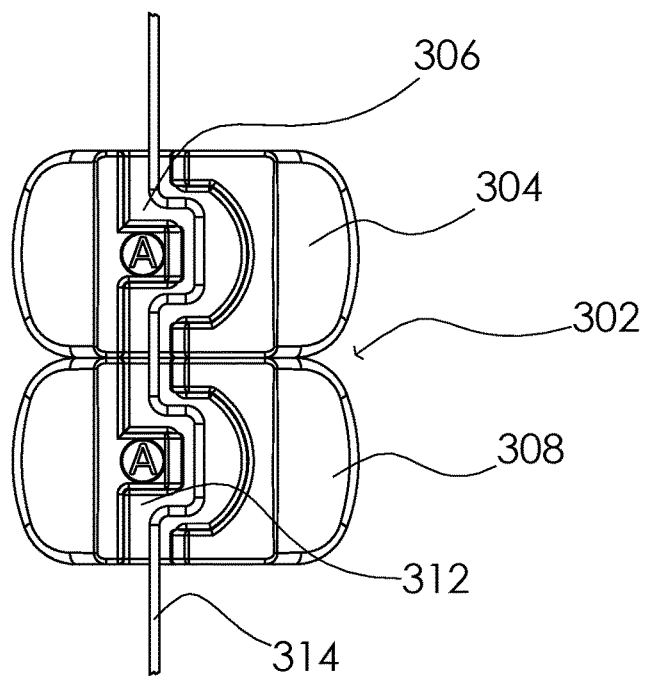

In another embodiment of the invention, a catheter management assembly or module 302 shown in FIG. 10C may comprise a medical holding unit 304 with a channel 306 and a medical holding unit 308 with a channel 312, to substantially increase the rotational and translational holding ability, for example, with regard to holding catheter 314. Medical holding units 304 and 308 may be separate members that are permanently or removably affixed to one another by glue or mechanical means or they may be manufactured as one continuous unit, or snapped together as in FIG. 10A.

Figure 10D:
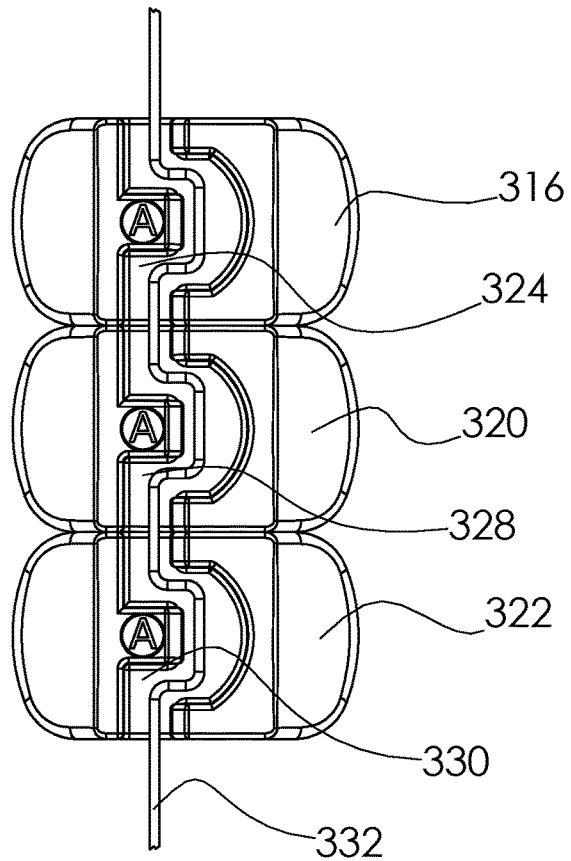

Each medical holding unit may have more than one channel, and assembly or module 302 may comprise more than two medical holding units, as shown in FIG. 10D. Medical holding units 316, 320, and 322 have channels 324, 328, and 330, respectively, to hold a catheter 332. It is within the scope of the invention that different medical holding units having different numbers of channels may be attached to one another to form an assembly or module.

Figure 11:
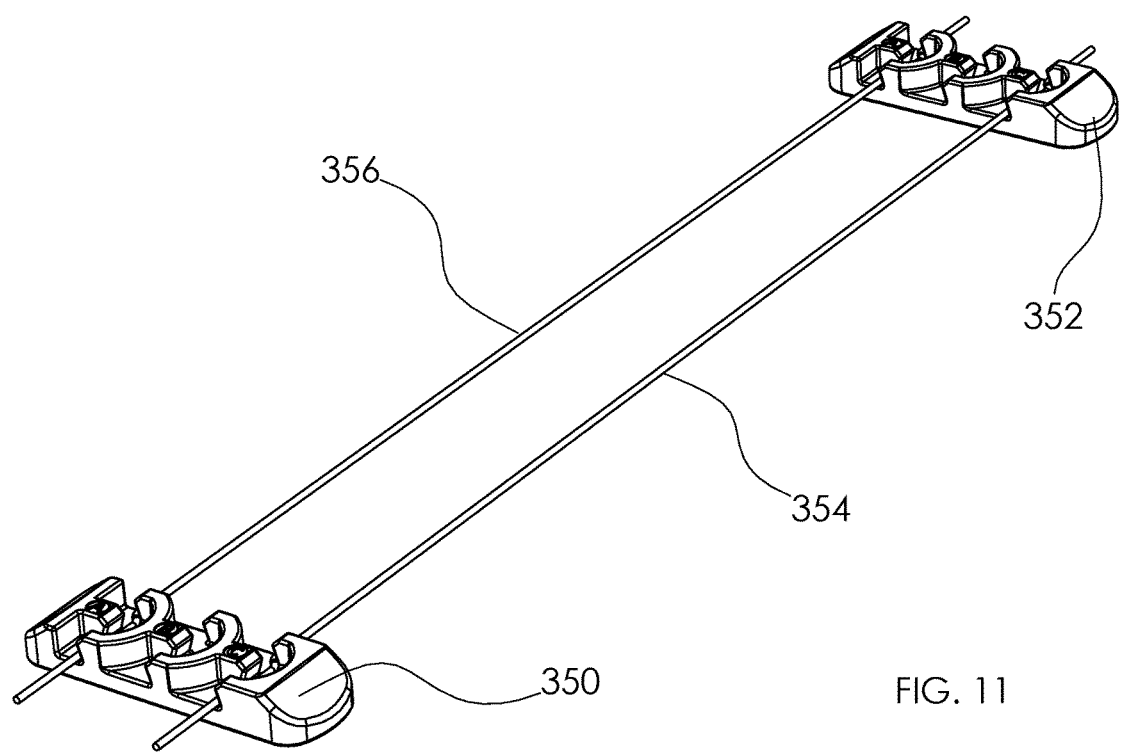
FIG. 11 is a schematic representation of a system of the invention comprising a system of two elongated medical device or member management systems.

In another aspect of the invention, there may be two or more medical device or catheter management systems or medical holding units arranged, for example, in parallel, about 1 to about 3 feet apart, to manage and separate two or more catheters, guide wires, sheaths, leads, or other elongated medical devices or members. See, for example, FIG. 11, where two substrates 350, 352 are arranged in parallel about two feet apart to manage catheters 354, 356.

It is within the scope of the invention that a medical holding unit or any assembly thereof may have a component that functions as a splitter to split, for example, a catheter, sheath, or lead. FIG. 12A is a top view, and FIG. 12B is a side or lateral view, of a medical holding unit 402 having a substrate 404 with three channels 406 and protrusions 408. Each of protrusions 408 has a letter, formed in a mold or applied to the protrusion, to identify an elongated medical device or member. A tab 412 of a flexible material 414 is attached to an adhesive layer 416 on the bottom surface 418 of substrate 404.

The lateral longitudinal surfaces 422 of substrate 404 each have a longitudinally extending ridge 424 for engagement by connector elements 448 of a splitter assembly 430. Alternatively, ridges 424 could be channels or tracks.

Figure 13A:
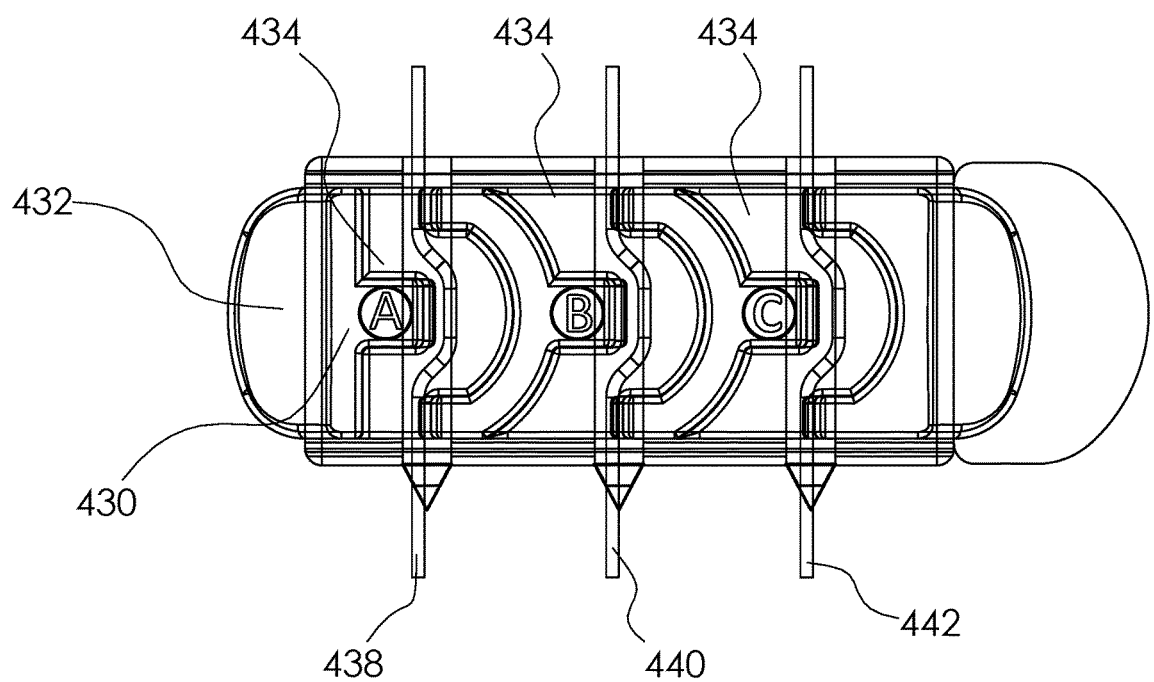
FIGS. 13A to 13D are schematic views of a splitter assembly attached to a substrate of a medical holding unit of the invention.

FIG. 13A is a top view of a clear plastic splitter assembly 430 that has been snapped into position on top of a substrate 432 with channels 434 having elongated medical devices or members 438, 440, 442, such as leads or sheaths, positioned therein. For example, the elongated medical devices 438, 440, and 442 could be a right ventricular lead, a left ventricular lead, and a right atrial lead, respectively. Splitter assembly 430 puts pressure from above on elongated medical devices 438, 440, and 442. Splitter assembly 430 has one or more, preferably one, metal cutting component 446 for cutting a catheter, sheath, or lead.

Figure 13B:
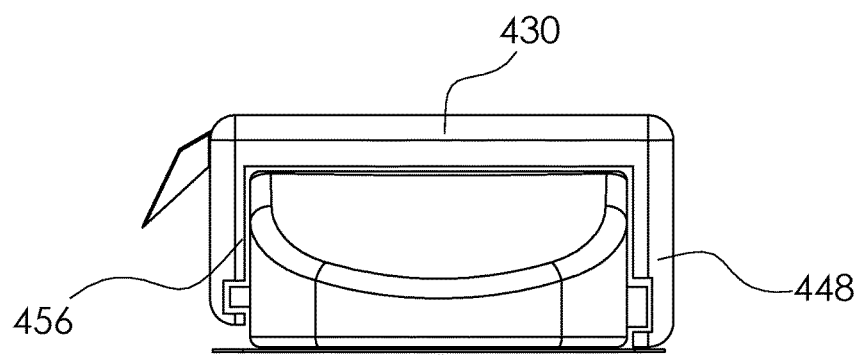
Figure 13C:
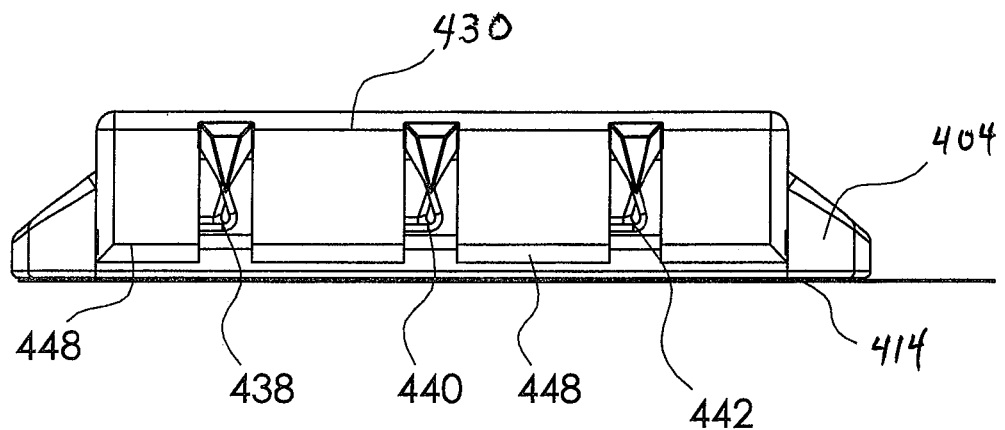

As shown in a front view of FIG. 13B, connectors 448 of splitter assembly 430 engage one of the ridges 424 of substrate 404. Similarly, as shown in the first lateral view of FIG. 13C, connectors 448 engage a ridge 424. Connectors 448 each have a tab to facilitate bending the splitter assembly 430 at ridge 424.

Figure 13D:
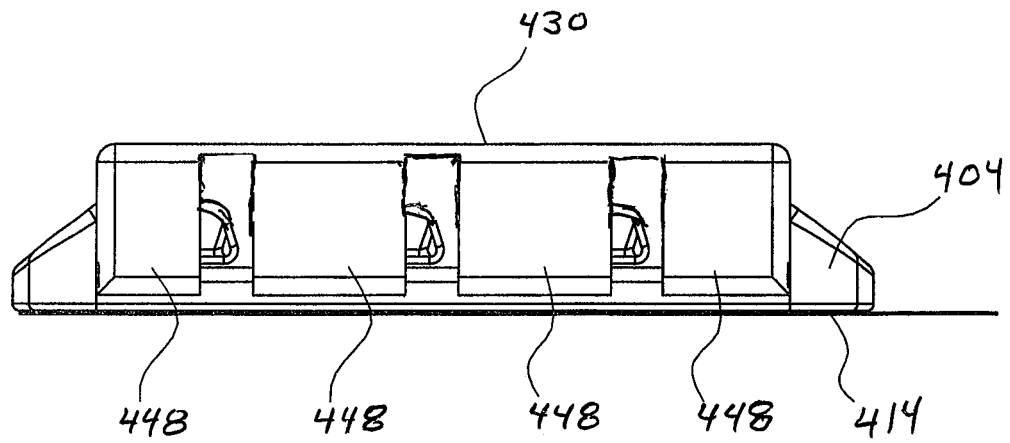

An opposite lateral view of splitter assembly 430 is shown in FIG. 13D, with tabs 448. The left tabs are lower than the right tabs to help bend the splitter assembly over ridge 424. The tabs form hooks, and a center blade is positioned for splitting.

The splitter assembly is preferably made from a firm but flexible, preferably clear, polymeric material. The splitter assembly may have indentations that correspond to the elongated medical devices or members. Also, the splitter assembly may be configured to be essentially any functional member that can attach to a holding unit and have a blade, hook, or other sharpened structure or other sharp component to split a sheath, catheter, or lead. This would include, for example, a sharpened blade that could be inserted into a hole or slot within the substrate itself.

Substrates of the medical device or catheter management systems described herein, especially in FIGS. 7A to 8, comprise a firm but flexible material, such as a silicone, cross-linked polydimethylsiloxane, or polysiloxane. Useful polymeric materials include, but are not limited to, SILASTIC® elastomers, available from Dow Corning.

An adhesive layer herein, such as adhesive layer 154, preferably comprises pre-formed adhesive tape that is sticky on both the upper and lower surfaces and has peel away protective tape (not shown) on both surfaces. One surface is exposed when the medical device or catheter management system is assembled; the other surface is exposed when the medical device or catheter management system is applied to a desired surface. Examples of adhesive tapes or substrates that are useful include 3M's 1587 and 1772 contact adhesives, which have a $\frac{1}{16}$" polyethylene foam substrate. Alternatively, direct adhesive could be applied to the bottom surface with protective peel-off tape with a tab to provide easy removal.

Channels of the substrates, such as channels 144, can be from about 0.2 to about 3.0 cm wide or deep, preferably from about 0.25 to about 2.0 cm wide or deep. This can vary, according to the operator's wishes, habits, or desires. Additional sizes and dimensions could be configured for microsurgical applications as well as macrosurgery.

The dimensions of the medical device or catheter management system or medical holding unit set forth in the drawings, especially in FIGS. 7A to 8, can vary greatly due to the intended application and the number of elongate medical devices that may be used. In one embodiment of the invention, the medical holding unit may have a length of from about 0.5 to about 10.0 inches, a width of from about 0.2 to about 5.0 inches, and a thickness of from about 0.1 to about 0.5 inches.

In one embodiment of the invention, the medical device or catheter management system or medical holding unit may comprise predetermined sizes of perhaps from about 2 to about 16, preferably from about 4 to about 12, inches in length. Optionally the catheter management system or medical holding unit may comprise longer lengths that can be cut to size, dependent upon the number of expected elongated medical devices or members. Alternatively, the medical device or catheter management system could be perforated or otherwise frangible at regular or irregular intervals so that lengths of useful size can be cut or torn off.

While the particular invention as herein shown and disclosed in detail is fully capable of obtaining the objects and providing the advantages hereinbefore stated, it is to be understood that this disclosure is merely illustrative of the presently preferred embodiments of the invention and that no limitations are intended other than as described in the appended claims.

We claim:

1. A sterile resistive medical holding apparatus, which comprises;
   a flexible, elongated, injection molded substrate having a slightly curved upper surface, at least one curvilinear channel comprising a resistance projection capable of holding and releasing an elongated medical device or member, and a slightly curved, adhesive lower surface substantially coplanar to the upper surface,
   wherein each of the at least one curvilinear channel has a depth perpendicular to the upper surface and has lateral surfaces substantially perpendicular to the upper surface,
   wherein the resistance projection has a depth corresponding to the depth of each of the at least one curvilinear channel and extends from about 10% to about 90% perpendicularly across each of the at least one curvilinear channel in a direction parallel to the upper surface, and
   wherein rotation and translation of the elongated medical device or member can be controlled and the elongated medical device or member can be easily removed when sufficient force is manually applied to the elongated medical device or member to release the elongated medical device or member from the sterile resistive medical holding apparatus for additional manipulation.

2. The medical holding apparatus of claim 1, wherein the medical holding apparatus is capable of holding and releasing the elongated medical device or member having different diameters.

3. The medical holding apparatus of claim 1, wherein the elongated medical device or member is selected from the group consisting of a catheter, a lead, a stylet, medical tubing, and a guide wire.

4. The medical holding apparatus of claim 1, wherein the at least one curvilinear channel has the depth and a width sufficient to receive and hold the elongated medical device or member.

5. The medical holding apparatus of claim 1, wherein the resistance projection is centrally located within the at least one curvilinear channel to provide resistance to rotation and translation of the elongated medical device or member.

6. The medical holding apparatus of claim 1, in which the at least one curvilinear channel comprises two or more channels aligned in parallel to hold and release each elongated medical device or member.

7. The medical holding apparatus of claim 6 in which each of the at least one curvilinear channel comprises variable width, depth, and location of the resistance projection to control the resistance of the elongated medical device or member based upon particular size of the elongated medical device or member.

8. The medical holding apparatus of claim 1, wherein the resistance projection extends from about 15% to about 80% perpendicularly across the at least one curvilinear channel.

9. The medical holding apparatus of claim 1, wherein the flexible substrate is an injection molded polymer or rubber.

10. The medical holding apparatus of claim 1, wherein the upper surface of the flexible substrate contains labeling either imprinted on or formed as part of the molded structure, to help organize the elongated medical device or member.

11. The medical holding apparatus of claim 1, wherein the lower adhesive surface comprises a biocompatible adhesive material capable of holding the medical holding apparatus against a patient's skin, a sterile medical drape, a patient's clothing, or a flat surface, proximal to an insertion site of the elongated medical device or member.

12. The medical holding apparatus of claim 1 which comprises an integral slitter capable of slitting and removing an introducer sheath from an implanted pacing or defibrillation lead while maintaining other previously implanted leads in position.

13. The medical holding apparatus of claim 12 which comprises an additional component contiguous to at least one channel opening which is capable of being inserted within the introducer sheath such that the introducer sheath itself can be easily removed while the implanted pacing or defibrillation lead is maintained in its previously placed position.

14. An assembly of medical holding apparatuses, wherein two or more sterile resistive medical holding apparatuses of claim 1 are arranged in series.

15. The assembly of claim 14, wherein the at least one curvilinear channel comprises two or more channels aligned to augment and enhance resistance of the elongated medical device or member to prevent further rotation and translation of said elongated medical device or member.

16. The assembly of claim 14, wherein the two or more medical holding apparatuses have lateral surfaces that can be permanently or releasably adjoined to hold the two or more medical holding apparatuses in place adjacent to each other.

17. The assembly of claim 14 which is capable of maintaining all inserted leads in position and allowing slitting of introducer sheaths and removal of said introducer sheaths.

18. A medical holding apparatus for managing one or more elongated medical devices or members, comprising:
   a flexible, elongated, injection molded substrate having a slightly curved upper surface, wherein the substrate has one or more curvilinear channels each extending from a first lateral surface to a second opposed lateral surface, and having a resistance projection capable of holding and releasing an elongated medical device or member, and a slightly curved, adhesive lower surface substantially coplanar to the upper surface,
   wherein each of the one or more curvilinear channels has a depth and has lateral surfaces substantially perpendicular to the upper surface,
   wherein the substrate has a bottom surface coplanar to the upper surface and one or more adhesive layers are attached to the bottom surface,
   wherein the resistance projection has a depth corresponding to the depth of each of the at least one curvilinear channel and extends from about 10% to about 90% perpendicularly across each of the at least one curvilinear channel in a direction parallel to the upper surface, and wherein each of the one or more curvilinear channels has a depth sufficient to receive one of the one or more elongated medical devices or members and each channel comprises curvature or a resistance projection to releasably hold one of the one or more elongated medical devices or members.

19. The medical holding apparatus of claim 18, wherein the substrate has two or more of the one or more curvilinear channels.

20. An assembly of two or more medical holding apparatuses of claim 18, wherein the two or more medical holding apparatuses are arranged parallel to one another, and separated but perpendicular to the one or more elongated medical devices or members to organize the one or more elongated medical devices or members and/or connector cables and to prevent entanglement of said one or more elongated medical devices or members.

21. The assembly of claim 20, wherein the two or more medical holding apparatuses have lateral surfaces that can be permanently or releasably adjoined to hold the two or more medical holding apparatuses in place adjacent to each other.

* * * * *